United States Patent
McKinley (10) Patent No.: US 6,981,973 B2
(45) Date of Patent: *Jan. 3, 2006

(54) LOW PROFILE VERTEBRAL ALIGNMENT AND FIXATION ASSEMBLY

(76) Inventor: Laurence M. McKinley, 355 E. Grand Ave., Suite 2, Escondido, CA (US) 92025

( * ) Notice: Subject to any disclaimer, the term of this patent is extended or adjusted under 35 U.S.C. 154(b) by 129 days.

This patent is subject to a terminal disclaimer.

(21) Appl. No.: 10/639,119

(22) Filed: Aug. 11, 2003

(65) Prior Publication Data

US 2005/0038430 A1   Feb. 17, 2005

(51) Int. Cl.
A61B 17/56 (2006.01)
A61F 2/30 (2006.01)

(52) U.S. Cl. .......................................... 606/61; 606/73
(58) Field of Classification Search ................... 606/60, 606/61, 72, 73
See application file for complete search history.

(56) References Cited

U.S. PATENT DOCUMENTS

| | | | |
|---|---|---|---|
| 5,207,678 A | | 5/1993 | Harms et al. |
| 5,360,431 A | | 11/1994 | Puno et al. |
| 5,443,467 A | | 8/1995 | Biedermann et al. |
| 5,466,237 A | | 11/1995 | Byrd, III et al. |
| 5,474,555 A | | 12/1995 | Puno et al. |
| 5,496,321 A | | 3/1996 | Puno et al. |
| 5,545,165 A | | 8/1996 | Biedermann et al. |
| 5,624,442 A | | 4/1997 | Mellinger et al. |
| 5,667,508 A | * | 9/1997 | Errico et al. ............... 606/73 |
| 5,672,176 A | | 9/1997 | Biedermann et al. |
| 5,697,929 A | | 12/1997 | Mellinger |
| 5,716,356 A | * | 2/1998 | Biedermann et al. ......... 606/61 |
| 5,725,527 A | | 3/1998 | Biedermann et al. |
| 5,882,350 A | | 3/1999 | Ralph et al. |
| 5,961,517 A | | 10/1999 | Biedermann et al. |
| 6,010,503 A | | 1/2000 | Richelsoph et al. |
| 6,132,432 A | | 10/2000 | Richelsoph |
| 6,132,434 A | | 10/2000 | Sherman et al. |
| 6,214,012 B1 | * | 4/2001 | Karpman et al. ............. 606/93 |
| 6,280,442 B1 | | 8/2001 | Barker et al. |
| 6,302,888 B1 | | 10/2001 | Mellinger et al. |
| 6,443,953 B1 | | 9/2002 | Perra et al. |
| 6,454,768 B1 | * | 9/2002 | Jackson ....................... 606/61 |
| 6,471,705 B1 | | 10/2002 | Biedermann et al. |
| 6,520,963 B1 | * | 2/2003 | McKinley ................... 606/61 |
| 2002/0058942 A1 | | 5/2002 | Biedermann et al. |

OTHER PUBLICATIONS

PCT International Search Report dated Dec. 4, 2003, from corresponding International Application PCT/US03/25196 filed Aug. 11, 2003.

PCT International Search Report dated Dec. 27, 2001, from corresponding International Application PCT/US01/41684 filed Aug. 13, 2001.

* cited by examiner

Primary Examiner—Eduardo C. Robert
Assistant Examiner—Anuradha Ramana
(74) Attorney, Agent, or Firm—Christie, Parker & Hale, LLP (57) ABSTRACT

A method and apparatus for aligning and fixing vertebral bodies is provided. The low profile vertebral alignment/fixation assembly of the current invention comprises a hemispherical headed pedicle screw disposed within a slotted coupling unit designed to allow angular adjustment of the pedicle screw up to 90° and which may be securely locked into position via a single internal locking nut once a standard alignment rod has been inserted into the slotted coupling unit. The low profile vertebral alignment/fixation assembly enabling the angular adjustment of the fixation system hardware after final placement and insertion of the pedicle screw into the vertebral body. A system and method for aligning and fixing vertebral bodies using the low profile vertebral alignment/fixation assembly of the invention is also provided.

18 Claims, 8 Drawing Sheets

LOW PROFILE VERTEBRAL ALIGNMENT AND FIXATION ASSEMBLY

FIELD OF THE INVENTION

The present invention relates generally to a method and apparatus for alignment and fixation of vertebral bodies.

BACKGROUND OF THE INVENTION

Pedicle screws allow spine surgeons to attach rods or plates to the thoracic and lumbar spine. This rigidly immobilizes the spine segments, promoting the bone graft to grow into a fusion, welding spinal segments into one solid unit, reducing pain and stabilizing deformity without requiring complete immobilization of the patient for the extended period of time during the healing process.

While many different pedicle screws have been developed, presently most pedicle screws are fixed axis devices which must be carefully aligned during insertion and fixation in the spine. Specifically, the screws must be drilled or screwed into the bone at a very specific angle to assure that the alignment hardware is exactly positioned such that the receiving portions of the fixation hardware are aligned so that the rod can be passed therethrough without distorting the screw or putting an undesirable level of stress on the attachment point. As a result, the alignment procedure requires a considerable amount of time, increasing the possibilities of complications during surgery and, in many cases the alignment fails and must be repeated. Further, the insertion of the screw is dependent on the angle of alignment required, resulting in insertions that are not in the most secure or safe positions with respect to the vertebral bodies.

The art contains a variety of pedicle screws which permit a level of freedom with respect to the alignment of the screw and the coupling element. However, these teachings have generally been complex, and inadequately reliable with respect to durability. The considerable drawbacks associated with the prior art systems include limited angular adjustability, complexity, difficult of properly positioning the coupling elements and the rod, tedious manipulation of the many parts associated with the complex devices and the considerable cost associated with manufacturing such complex mechanisms.

Accordingly, a need exists for an inexpensive, durable and simple vertebral alignment assembly that allows a surgeon to freely manipulate the alignment of the coupling hardware such that the fixation rods can be properly positioned with respect to the vertebral bodies without a time consuming and potentially dangerous alignment procedure.

SUMMARY OF THE INVENTION

The present invention relates generally to a method and apparatus for aligning and fixing vertebral bodies. More specifically, the present invention is directed to a low profile vertebral alignment/fixation assembly and method which allows a surgeon to manipulate and align the unit coupling the fixation hardware with the pedicle screw, the assembly comprising a hemispherical headed pedicle screw disposed within a slotted coupling unit designed to allow angular adjustment of the pedicle screw up to 90° and which may be securely locked into position via a single internal locking nut once a standard alignment rod has been inserted into the slotted coupling unit. The low profile vertebral alignment/fixation assembly enabling the angular adjustment of the fixation system hardware after final placement and insertion of the pedicle screw into the vertebral body.

In one embodiment, the low profile vertebral alignment/fixation assembly of the current invention generally consists of three main components: a hemispherical pedicle screw, a slotted coupling unit designed to receive the pedicle screw and an alignment rod, and an internal securing nut for fixing the angular position of the coupling unit and the position of the alignment rod within the coupling unit.

In one alternative exemplary embodiment, the pedicle screw of the invention has a slotted tip to allow the screw to self-tap the vertebral body and thereby ease the insertion of the screw into the bone.

In another exemplary embodiment the portion of the internal securing nut which engages the alignment rod is textured to provide a more secure grip of the alignment rod.

In still another exemplary embodiment the internally securing nut has an annular channel disposed such that a screw driver can be inserted therethrough and interact with the pedicle screw to drive the screw into a vertebral body.

In yet another exemplary embodiment the pedicle screw is provided with a square opening in its hemispherical head such that a square headed driving tool can be mated therewith to drive the screw into the vertebral body.

In still yet another exemplary embodiment the components of the system are made from an orthopaedically suitable material, such as, for example, stainless steel or titanium.

In still yet another preferred embodiment, the invention is directed to a system for aligning and fixing vertebral bodies comprising a multiplicity of vertebral alignment components as described above attached at suitable points of attachment as determined by the deformity of the spine.

In still yet another embodiment, the invention is directed to a method for aligning vertebral bodies. The method comprises manipulating, aligning and fixing the spine using a vertebral alignment system as described above.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The present invention relates generally to a method and apparatus for aligning and fixing vertebral bodies. More specifically, the present invention is directed to a system and method which allows a surgeon to manipulate the angular alignment of the fixation hardware of a low profile vertebral alignment/fixation system after insertion and fixation of the pedicle screws into the vertebral bodies using freely rotatable couplers mounted to hemispherical pedicle screws. The system and method is further designed to enable the fixation of the angular alignment and installation and fixation of the alignment rods to the couplers by application of a single internal securing nut.

As shown in FIGS. 1 to 5, the low profile vertebral alignment/fixation assembly 10 of the current invention, hereinafter referred to simply as a vertebral alignment/fixation assembly consists of three main components: a hemispherical pedicle screw 12, a coupler unit 14 which functions as a universal joint, and an internal securing nut 16.

Figure 1:
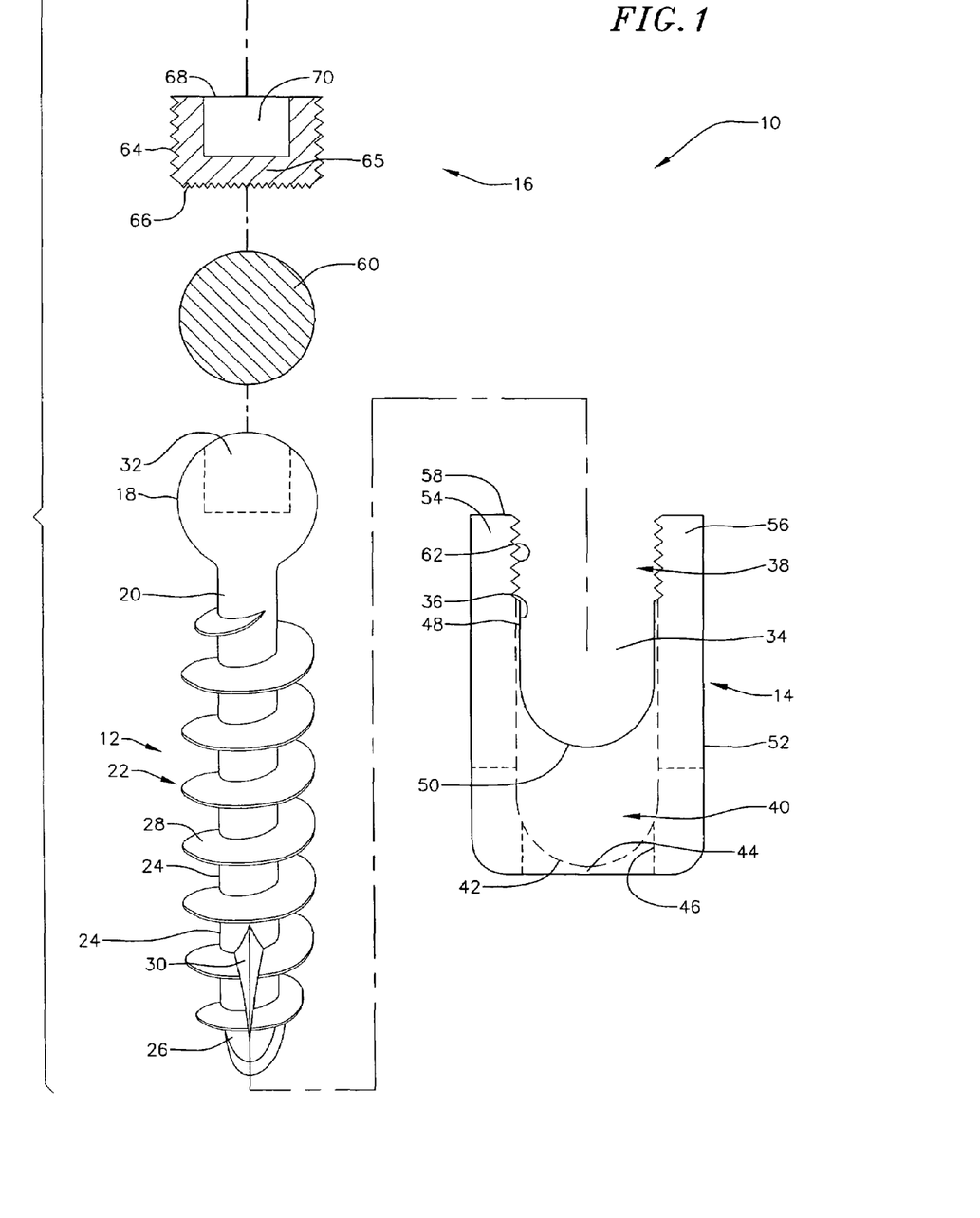
FIG. 1 is a side view of an embodiment of an unassembled pedicle screw according to the invention.

The hemispherical pedicle screw 12, as shown in FIG. 1, comprises a substantially hemispherical head portion 18, a neck portion 20 and a shaft portion 22. Although in FIG. 1 the shaft 22 is shown as having a generally cylindrical body 24 and a tapered tip 26 with a thread 28 dispose along the length of the shaft 22, any shaft design, thread pitch or tip taper suitable for insertion into a vertebral body can be utilized in the current invention. In the embodiment shown in FIG. 1, the tapered tip 26 of the pedicle screw shaft 22 further comprises a slotted groove 30 running longitudinally along the shaft, designed such that the screw is self-tapping easing the insertion of the pedicle screw 12 into the vertebral body.

The head portion 18 of the pedicle screw 12 comprises a substantially hemispherical shape. The substantially hemispherical shape of the head portion 18 of the screw 12 is a portion or section of a sphere. Although in the embodiment shown, the section or portion of the sphere comprising the head 18 of the screw 12 is greater in extent than a hemisphere, it should be understood that any external contour which is equidistant from a center point of the head portion 18 could be utilized. In the embodiment shown in FIG. 1, the major cross-section of the substantially hemispherical head portion 18 includes at least 270 degrees of a circle.

Figure 4A:
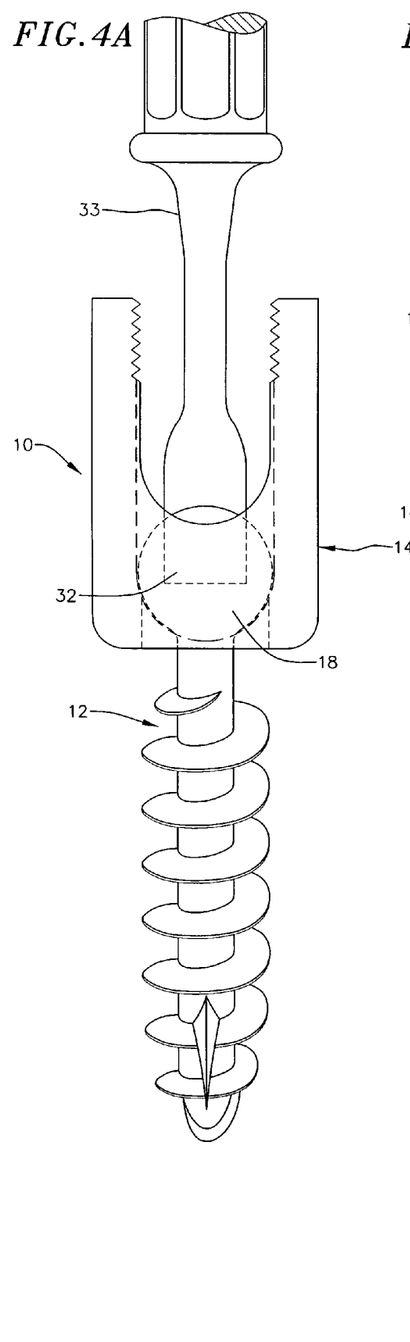
FIG. 4a is a side view of the interrelation of an embodiment of a pedicle screw and screw driver according to the invention.
Figure 4B:
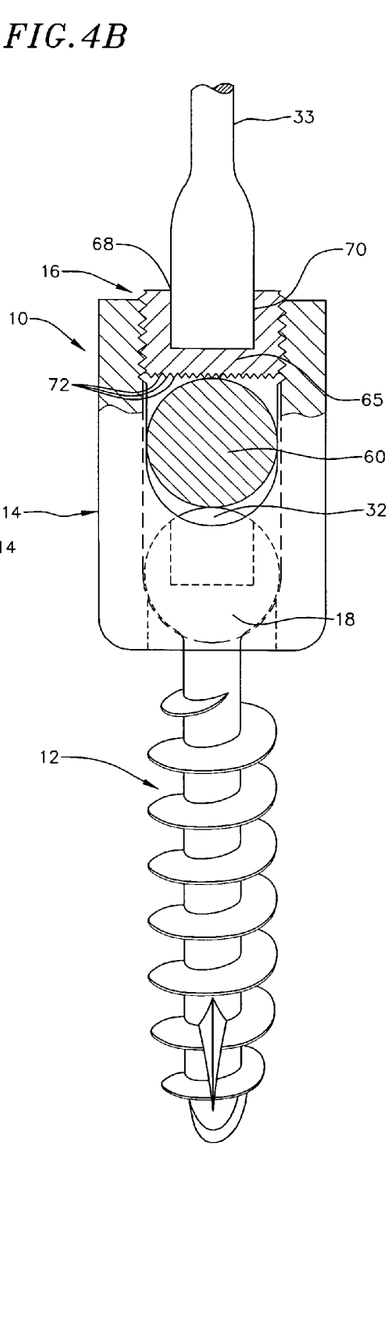
FIG. 4b is a cross section of the interrelation of an embodiment of a pedicle screw and screw driver according to the invention.

The hemispherical head portion 18 also has a recess 32 disposed therein (shown in phantom in FIG. 1). The recess 32 defines a engagement point for the application of torque from a torque driving tool 33 for driving the screw 12 into a bone. The specific shape of the recess 32 may be chosen to cooperate with any suitable screw-driving tool 33, as shown in FIGS. 4a and 4b. For example, the recess 32 may comprise a slot for a flat-headed screwdriver, a crossed recess for a phillips head screwdriver, a hexagonally shaped hole for receiving an allen wrench, or a "figure-8" shaped driver. In a preferred embodiment, a square-headed hole for a square screwdriver or socket-type wrench is utilized.

Although the recess 32 is shown to be co-axial with the general elongate axis of the screw shaft 22, it should be understood that any arrangement of recess 32 and screw 12 can be utilized such that sufficient torque may be applied to the screw 12 to drive it into a bone.

Figure 2A:
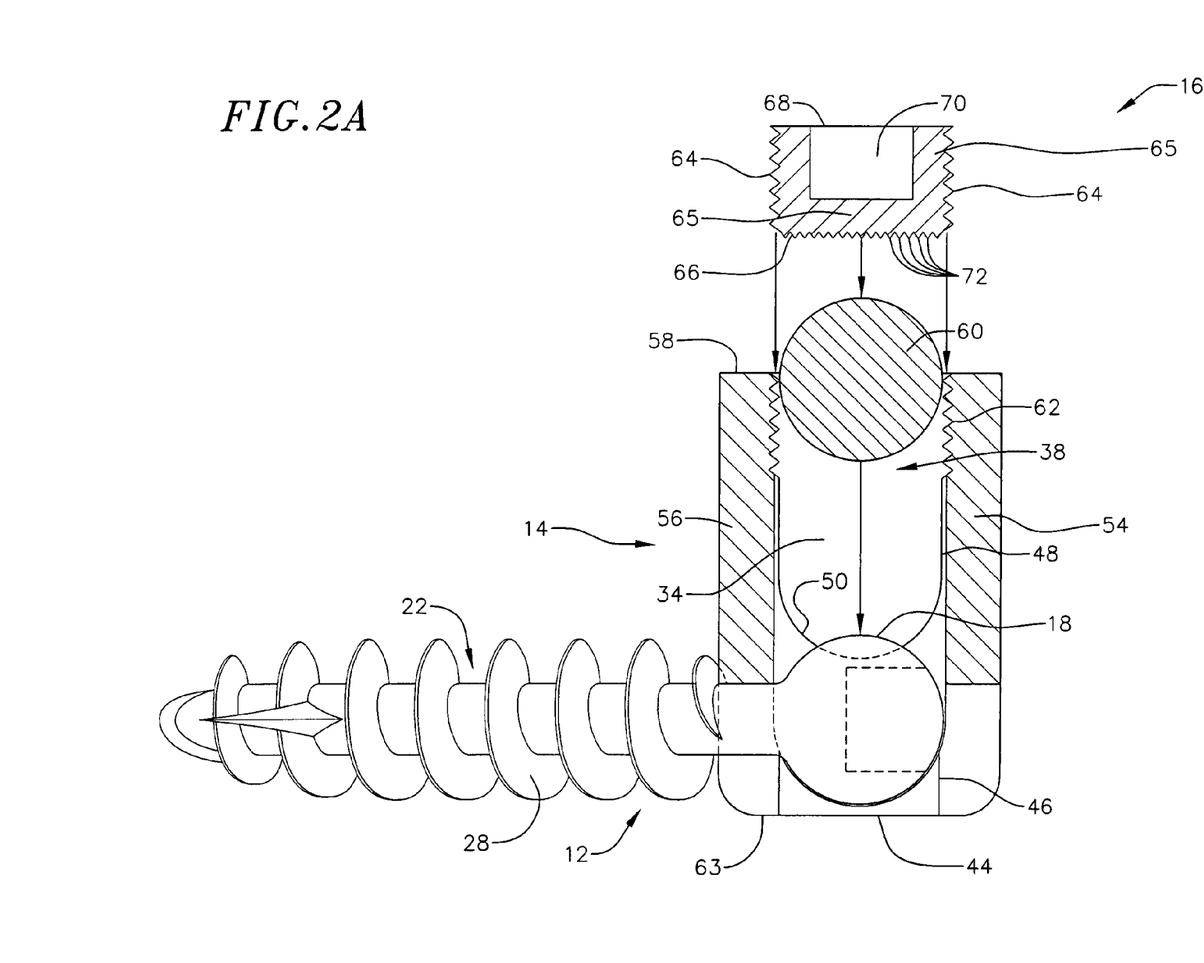
FIG. 2a is a side view of an embodiment of a partially assembled pedicle screw according to the invention.
Figure 2B:
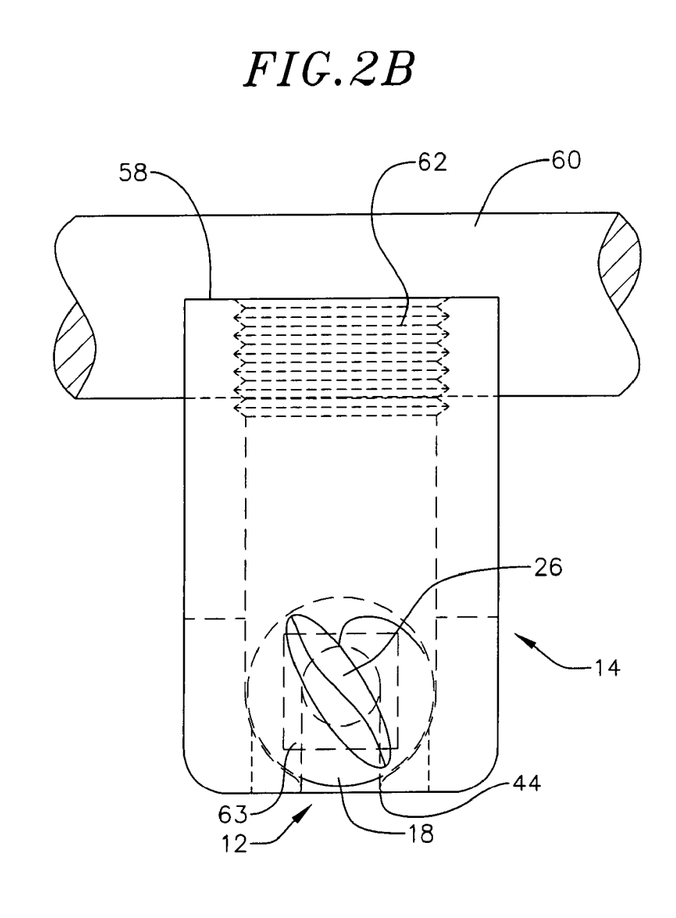
FIG. 2b is a front view of an embodiment of a partially assembled pedicle screw according to the invention.
Figure 2C:
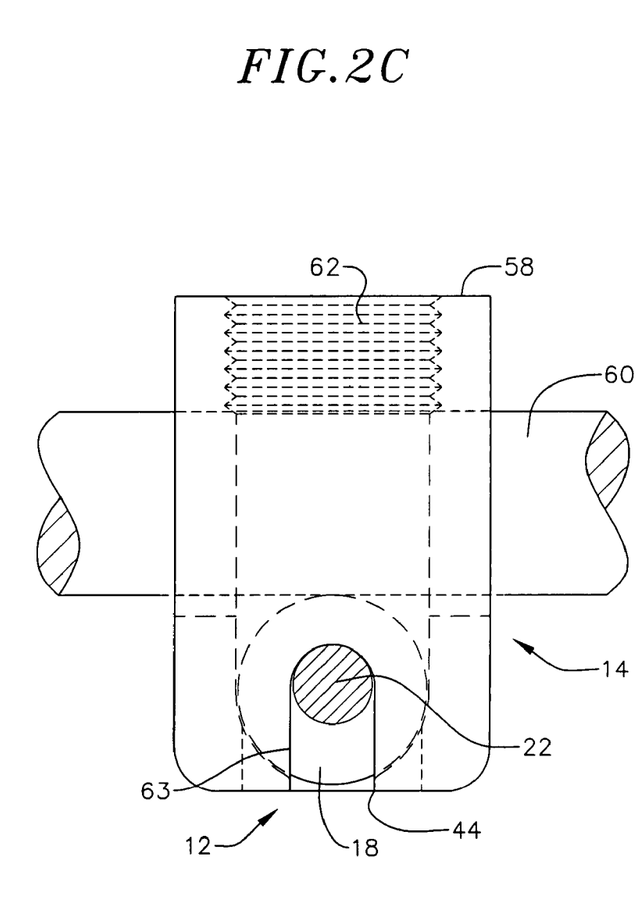
FIG. 2c is a front partial cross-sectional view of an embodiment of a partially assembled pedicle screw according to the invention.
Figure 5:
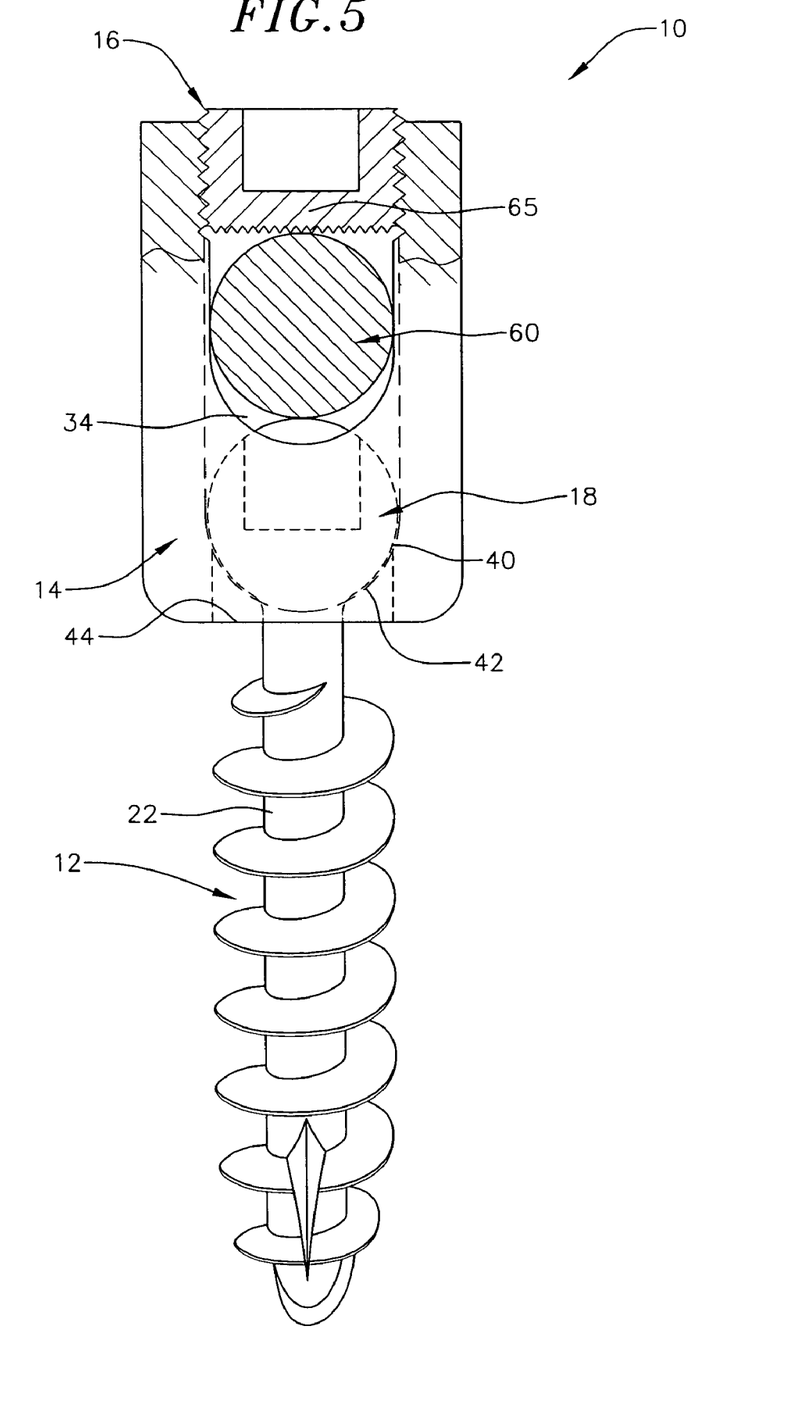
FIG. 5 is a side view of an assembled pedicle screw according to the invention.

The head portion 18 of the screw 12 is connected to the shaft portion 22 at a neck portion 20. In relation to each other, the diameter of the shaft 22 should be less than the diameter of the semi-spherical head 18, and the neck 20 of the screw 12 should be preferably narrower than the widest portion of the shaft 22. A pedicle screw 12 according to the invention having such dimensional relationships is preferable because the screw may be locked at a variety of angles with relation to the coupling unit 14 while still being securely joined to the coupling element 14 (embodiments of which are shown in FIGS. 1, 2 and 5). Although any biocompatible material having suitable strength and durability characteristics may be utilized, the pedicle screw 12 is preferably made from surgical grade titanium or stainless steel.

One exemplary embodiment of the universal joint coupling element 14 of the present invention is shown in a side view in FIG. 1, critical elements are shown in phantom. The coupling element 14 comprises a generally cylindrical tubular body which defines an inner passage 34 having an inner wall 36. The inner passage 34 comprises an upper generally cylindrical portion 38 and an inwardly curved lower portion 40. The inwardly curved lower portion 40 defines a socket, into which the head 18 of the screw 12 may rotatingly engage. The bottom surface 42 of the coupling element 14 includes an opening 44 defining a passage 46 such that the shaft 22 of the screw 12 may extend therethrough and pass outside the body of the coupling element 14. To securely engage the screw 12 within the coupling element 14, the dimensions of the opening 44 and passage 46, must be greater than the diameter of the shaft 22 of the screw 12, but less than the largest diameter of the head 18. The bottom surface 42 of the universal coupling element 14 is designed to have a rectangular configuration, as shown in FIG. 1, such that the maximum amount of supporting metal is provided to the coupling element to decrease the chances that the opening 44 would undergo spreading under heavy loads that might lead to a failure of the entire universal coupling element 14 and the release of the screw head 18 through the opening 44 and passage 46.

The cylindrical upper portion 38 of the coupling element 14 includes a pair of vertically oriented, channels 48 having rounded bottom surfaces 50 and open top portions disposed on opposing sides of the coupling element 14. In combination the channels 48 form engagement point for an elongated fixation rod 60. In addition the channels 48 divide the wall 52 of the coupling element 14 into upwardly extending members 54 and 56. As shown in the embodiment illustrated in FIGS. 1, 2 and 5, the vertical distance from the top 58 of the channels 48 to the curved bottom 50, is sufficient to allow the rod 60 which is to be provided to slidingly engage therein such that the rod 60 may be fully nested in the channels 48, but not any longer than necessary such that the maximum amount of supporting metal is provided to the coupling unit to decrease the chances that the opening 44 would undergo spreading under heavy loads that might lead to a failure of the entire universal coupling element 14 and the release of the screw head 18 through the opening 44 and passage 46.

In addition, the curved bottom 50 of the channels 48 are arranged such that the top of the head 18 of the screw 12, when fully nested in the lower socket portion 40, extends above the edge of the curved bottom 50 of the channels 48 such that a rod 60 positioned therein will pressingly engage the head portion 18 of the screw 12. The top 58 of the upper portion 38 of the coupling element 14, which comprises upwardly extending members 54 and 56, have disposed thereon a threading 62. The upper portion 38, and the threading 62 thereon, is ideally suited for threadingly engage a securing nut 16.

FIGS. 2a, 2b and 2c show an additional feature of one exemplary embodiment of the invention, which allows angular alignment of the screw 12 up to at least a 90 degree angle with respect to the coupling element 14. In this embodiment the lower portion 40 of the coupling unit 14 further comprises a pair of lower slots 63 extending from the opening 44 and passage 46 in the bottom surface 42 of the coupling unit 14. The lower slots 63 are aligned on opposite sides of the bottom surface 42 of the coupling unit 14 such that in combination the slots 63 define a single 180 degree passage dimensioned to allow the neck portion 20 of the screw 12 to move therein when the head portion 18 of the screw is fully engaged in the socket 40 of the coupling unit 14 and the coupling unit 14 is properly oriented with respect to the shaft 22 of the screw 12. As shown, even in this extreme angular position, the coupling unit 14 is designed such that a rod 60 inserted into the channels 48 will press against the head portion 18 of the screw 12 and at the urging of the internal securing nut 16 engage and fix both the rod 60 and in turn the coupling unit 14 into alignment.

Figure 3A:
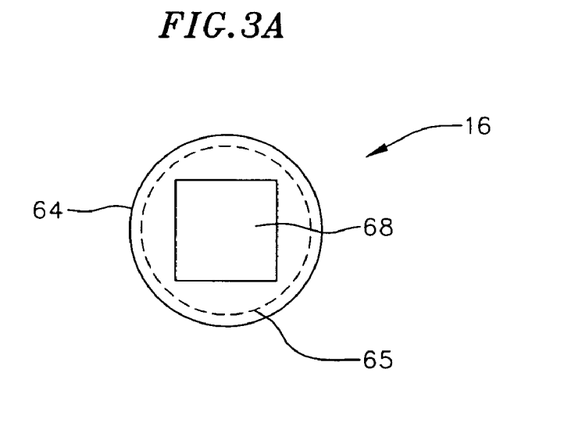
FIG. 3a is a top view of an embodiment of an internal securing nut according to the invention.
Figure 3B:
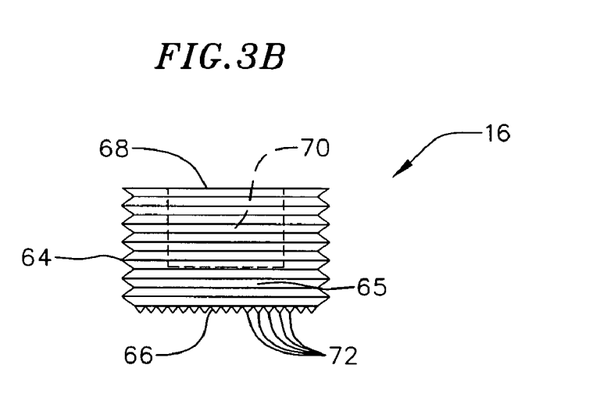
FIG. 3b is a cross section of an embodiment of an internal securing nut according to the invention.
Figure 3C:
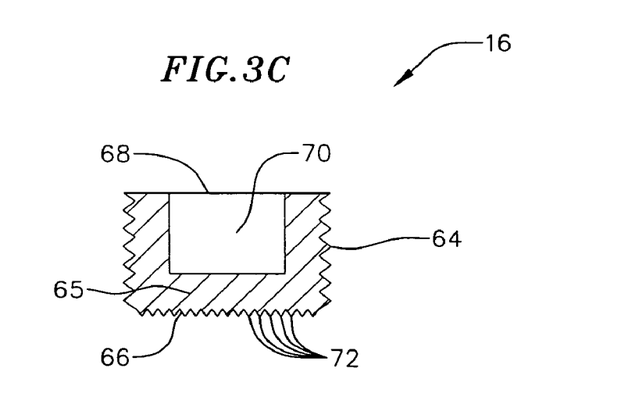
FIG. 3c is a side view of an embodiment of a securing nut according to the invention.

The top internal securing nut 16 is shown in top view in FIG. 3a, in side view in FIG. 3b, and in cross section in FIG. 3c. The internal nut is designed to fit entirely within the radial dimensions of the internal passage 34 of the coupling element 14 to provide a lower profile of exposure to the body of the patient than is obtained with a conventional external cap nut. As shown, although the internal nut 16 should not extend radially beyond the walls of the coupling unit 14, depending on the dimensions of the rod 60, some portion of the nut may extend above the top surface 58 of the coupling unit 14. The internal nut 16 itself comprises an outer threading 64, which is intended to mate with the internal threading 62 on the upwardly extending members 54 and 56 of the upper portion 38 of the coupling element 14. The nut 16 also comprises a plug portion 65 having a bottom surface 66 which is intended to seat against the top surface of the rod 60 seated in the coupling element 14, providing a means for driving the rod 60 downward and against the head portion 18 of the screw 12. A central annular opening 68 is provided in the center of the nut 16 defining a passage 70 passing therethrough, the passage 70 and opening 68 being designed such that the screw driver utilized to drive the screw 12 into the vertebral body can fit therein and can be utilized to tighten the nut 16 onto the coupling unit 14, as shown in FIG. 4b. Although the embodiment of the passage 70 shown in FIGS. 3a to 3c terminates in the middle of the plug 65 of the nut 16, the passage 70 could also transect the plug 65 forming a conduit between the opening 68 and the bottom surface 66.

In the preferred embodiment shown in FIG. 1, the bottom surface 66 of the internal nut 16 further comprises a plurality of raised metal teeth 72 designed to bitingly engage and press into the rod 60 providing additional frictional engagement between the rod 60 and the vertebral alignment assembly 10 such that the possibility of a mechanical shock jarring the rod 60 loose from the vertebral alignment assembly 10 is reduced. In another preferred embodiment, the rod 60 is manufactured with a rolled or corrugated finish to improve the frictional engagement between the rod 60 and the teeth 72 on the bottom surface 66 of the internal nut 16.

FIGS. 4a and 4b show the engagement of a driver 33 with the vertebral alignment assembly 10 to first engage the screw 12 into the vertebral body 74, as shown in FIG. 4a, and then to engage the internal securing nut 16 onto the coupling unit 14, as shown in FIG. 4b. As shown in FIG. 4a, the coupler unit 14 is designed such that the screw driver 33 can fit inside the inner passage 34 of the coupler 14 and engage the recess 32 of the head portion 18 of the screw 12 to drive the screw 12 into the vertebral body 74. As shown in FIG. 4b, the internal securing nut 16 is further designed such that the screw driver 33 can engage nut opening 68 to secure the internal nut 16 on the coupling unit 14 and thereby fix alignment rod 60 into coupling unit 14 and further secure the alignment of the coupling unit 14 in relation to the axis of the screw 12.

Referring now to FIG. 5, the coupling element 14 is shown with the screw 12 inserted therethrough, and the head 18 of the screw 12 nested in the lower socket portion 40 of the coupling element 14. The shaft portion 22 of the screw 12 is inserted downward, through the interior passage 34 of the coupling element 14, and out through the opening 44. In this position, the curved undersurface of the head portion 18 rests against the inwardly curved bottom surface 42 of the lower socket portion 40, and is prevented from translating further downward by the dimensions of the opening 44. Meanwhile, the uppersurface of the head portion 18 is pressed against the rod 60 which is pressed into the head portion 18 by the internal securing nut 16 thereby simultaneously preventing the rod 60 from moving out of the coupling unit 14 and preventing the coupling unit 14 from moving relative to the screw 12.

Figure 6:
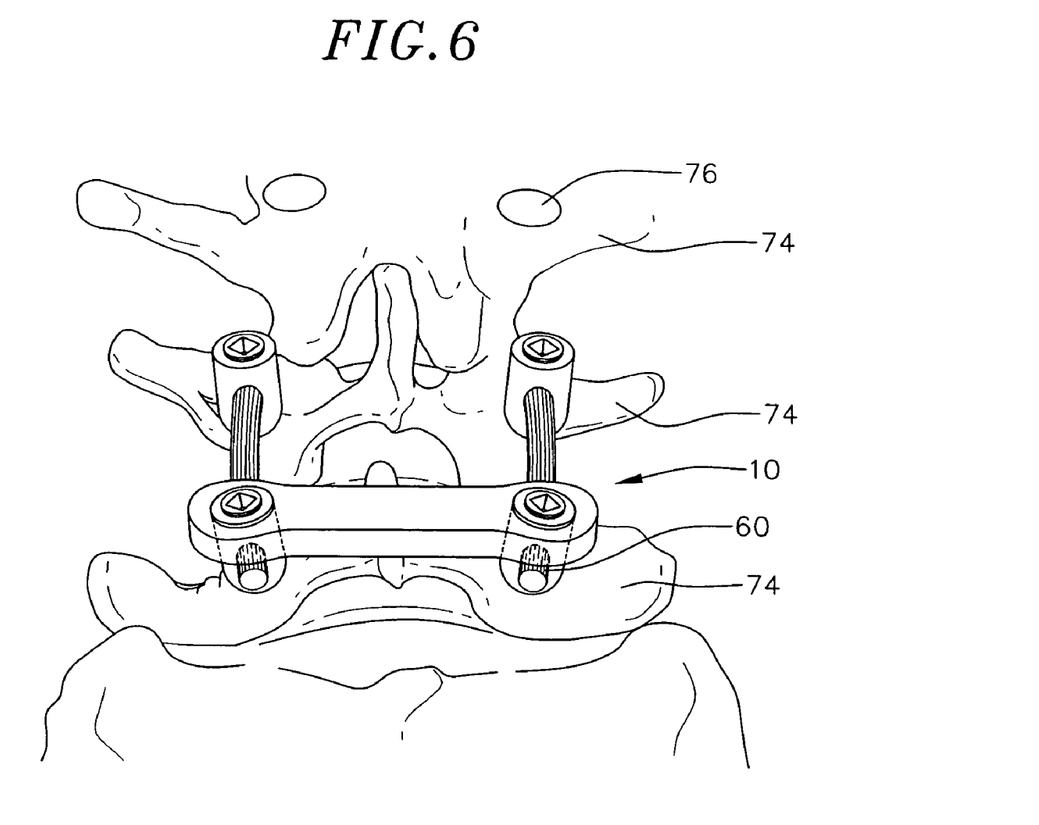
FIG. 6 is a schematic view of the manipulation and alignment of the spine utilizing an embodiment of the low profile vertebral alignment/fixation system according to the invention.
Figure 7:
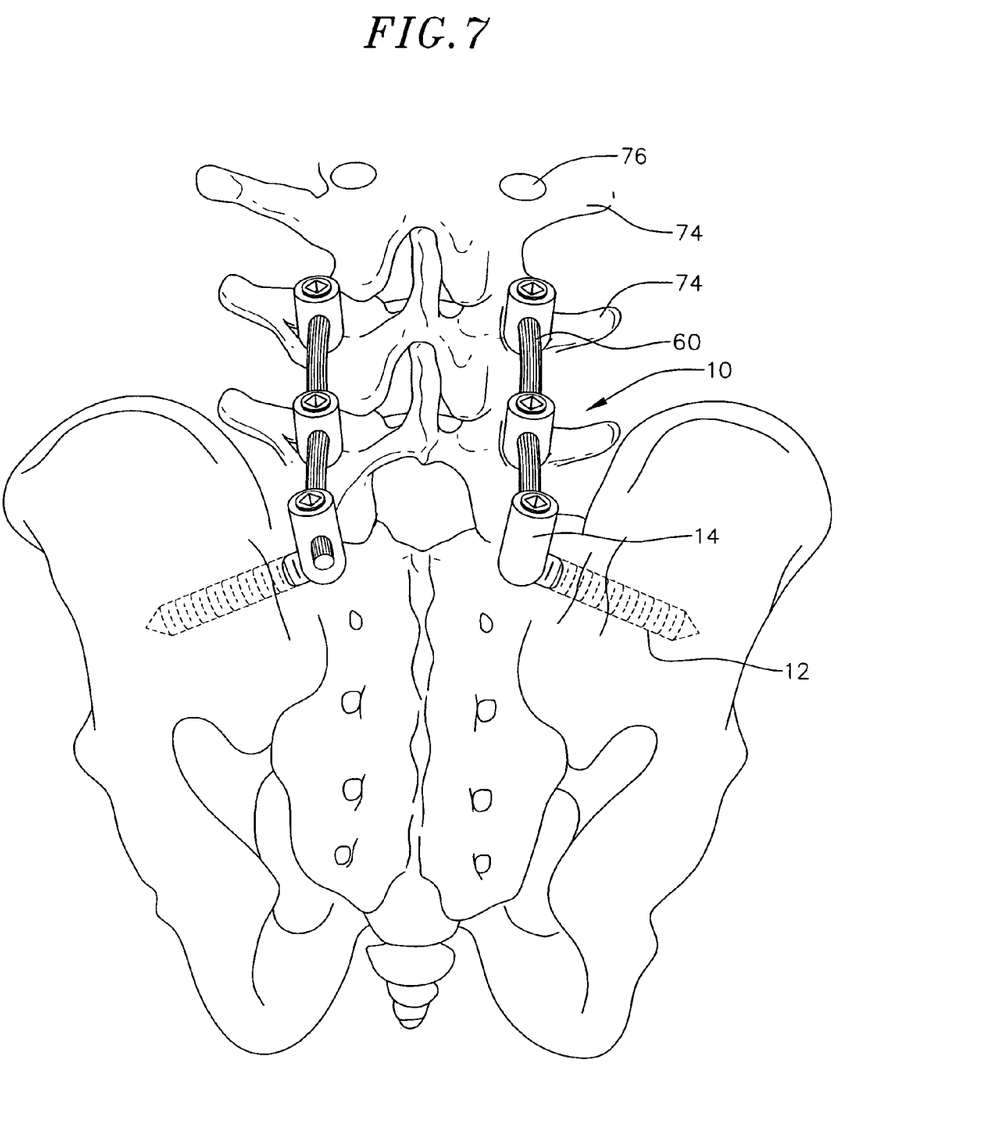
FIG. 7 is a schematic view of the manipulation and alignment of the spine utilizing an embodiment of the low profile vertebral alignment/fixation system according to the invention.

FIGS. 6 and 7, show a side view of the fully locked coupling element, rod, and screw system in relation to a vertebral body 74. FIG. 6 shows the vertebral alignment/fixation assembly 10 of the invention anchored traditionally in a plurality of vertebral bodies with an optional crosslink stabilizing bar. FIG. 7 shows the vertebral alignment/fixation assembly 10 of the invention anchored into the ileum bone with the screw 12 aligned at a 90° angle with reference to the coupling unit 14. With reference to these Figures, the preferred method of assembly and alignment of vertebral bodies is described.

First, a pre-drilled hole 76 is provided in the bone 74, into which the screw 12 is to be anchored. The hole 76 may be pretapped, or, as described above, the external threading 28 at the tip portion 24 of the screw 12 may include a self-tapping slot 30. In either case, during assembly, the tip 26 of the screw 12 is inserted through the interior passage 34 of the coupling element 14 until the shaft 22 of the screw 22 extends out of the coupling element 14 and the head 18 of the screw 12 is engaged in the lower socket portion 40 of the coupling unit 14. At this point in the assembly process, the coupling element 14 has the capacity to rotate relative to the screw 12. A screw-driving tool 33 is then aligned with the recess 32 in the head 18 of the screw 12 so that it may be driven into the preformed hole 76 in the bone 74.

After the screw 12 has been driven into the hole 76, the coupling element may be rotated relative to the screw 12, to align the coupling element 14 such that a support rod 60 may be engaged within the rod receiving channel 48 and properly aligned according to the surgeon's wishes. As shown best in FIG. 5, and previously discussed, the bottom of the rod 60 seats on the top of the head portion 18 of the screw 12, and not fully on the bottom curved surface 50 of the channels 48.

After the rod 60 is positioned within the coupling element 14, the internal locking nut 16 is threaded onto the threading 62 of the upwardly extending members 54 and 56. The internal locking nut 16 is then screwed down onto the coupling element 14 until the lower surface 66 of the engaging portion 65 of the internal locking nut 16 seats against the top surface of the rod 60. As the internal locking nut 16 descends onto the coupling element 14, the rod 60 is driven downward by the engaging portion 65 of the internal locking nut 16, causing the rod 60 to engage the head 18 of the screw 12 and to push the head portion 18 of the screw 18 downward pressingly engaging it within the socket 40 of the coupling element 14. This downward translation permits the bottom of the rod 60 to seat against the bottom surface 50 of the channels 48, and causes the head 18 of the screw 12 to be crush locked to the inwardly curved surface 40 of the coupling element 14. The force also engages the teeth 72 of the internal locking nut 16 into the rod 60 providing additional frictional engagement between the coupling element 14 and the rod 60. As such, the downward force of the bottom surface 66 of the internal locking nut 16 against the rod 60, as well as the teeth 72 and the counter-force provided by the bottom surface 50 of the channels 48 causes the rod 60 to be locked. This locking prevents the rod 60 from sliding relative to the assembled vertebral alignment assembly 10, locking the rod 60 to the coupling element 14, as well as the screw 12 to the coupling element 14.

In addition to these basic components, fixation hardware could also be provided to fix the spine into the desired alignment. The fixation hardware may comprise clamps, which are designed to mate with the top or side of the pedicle screw, bendable fixation rods or plates, which run between the clamps on the various pedicle screws attached either to different vertebral bodies or at different points on a single vertebral body, and bolts, also designed to mate with the clamps such that the clamps can be tightened onto and fix the fixation rods into place. In addition, as shown in FIG. 6 the fixation hardware may comprise crosslinks of any design suitable for attachment to the alignment assembly 10 of the current invention. For example, although the crosslink shown in FIG. 6 is of fixed dimension, slotted crosslinks may also be used for applications in which the distance between the fixation points of the crosslink must be changed. In such an embodiment, the openings in the crosslink for attaching it to the alignment assembly 10 (which are shown as simple holes in FIG. 6) comprise elongated slots such that the crosslink may be slid relative to the alignment assembly 10 along the length of the slot, thereby allowing for some degree of adjustment in the position of the crosslink relative to the alignment assembly.

All of the above components, including the fixation hardware can be made of any suitable surgical material, such as, for example, stainless steel or titanium.

Although specific embodiments are disclosed herein, it is expected that persons skilled in the art can and will design alternative low profile vertebral alignment/fixation screws that are within the scope of the following claims either literally or under the Doctrine of Equivalents.

What is claimed is:

1. A low profile vertebral alignment/fixation assembly comprising:
   a screw comprising an elongated threaded shaft defining a screw axis with a substantially hemispherical head having a driver engaging recess disposed therein arranged at one end of the shaft and a tapered tip arranged at the other end of the shaft;
   a coupling element comprising a cylindrical body having an internal threading disposed on said upper surface and defining an axial bore through which said screw may be inserted, said bore having a narrowing inwardly curved lower surface defining a socket designed to engage the substantially hemispherical head of the screw such that the head of the screw is prevented from passing therethrough and such that the screw may be rotated therein to adjust the angle between the axis of the screw and the axis of the bore, said coupling element further comprising a pair of opposing upper channels formed in the top of said coupling element such that an elongated rod may be received therein and a pair of opposing lower channels formed in the bottom of said coupling element designed to allow the shaft of the screw to move therethrough, the lower channels being designed such that the angle between the axis of the screw and the axis of the coupling element can be adjusted to at least 90 degrees; and
   a securing nut, mateable with said internal threading and entirely within at least the radial boundaries of the axial bore of said coupling element, the nut having an engaging portion designed to engage the elongated rod, the engaging portion further comprising a plurality of engaging teeth designed to frictionally lock the rod within the upper channel of the coupling element.

2. A low profile vertebral alignment/fixation assembly as described in claim 1, wherein the angles between the axis of the screw and the axis of the coupling element can be adjusted to at least 100 degrees.

3. A low profile vertebral alignment/fixation assembly as described in claim 1, wherein the assembly is made of stainless steel.

4. A low profile vertebral alignment/fixation assembly as described in claim 1, wherein the recess is designed to receive a screw driver from the group consisting of: flat-headed, phillips head, allen wrench, and square headed.

5. A low profile vertebral alignment/fixation assembly as described in claim 1, wherein the nut further comprises an axial recess identical to the recess disposed on the screw head.

6. A low profile vertebral alignment/fixation assembly as described in claim 5, wherein the nut recess is designed to receive a screw driver from the group consisting of: flat-headed, phillips head, allen wrench, and square headed.

7. A low profile vertebral alignment/fixation assembly as described in claim 1, wherein the screw further comprises a slotted groove disposed longitudinally along the tip and designed to allow the screw to be self-tapped.

8. A low profile vertebral alignment/fixation method comprising utilizing a plurality of vertebral alignment/fixation assemblies as described in claim 1 to align at least one vertebral body.

9. A low profile vertebral alignment/fixation system comprising:
   at least one elongated rod; and
   at least one vertebral alignment/fixation assembly comprising:
      a screw comprising an elongated threaded shaft defining a screw axis with a substantially hemispherical head having a driver engaging recess disposed therein arranged at one end of the shaft and a tapered tip arranged at the other end of the shaft,
      a coupling element comprising a cylindrical body having an internal threading disposed on said upper surface and defining an axial bore through which said screw may be inserted, said bore having a narrowing inwardly curved lower surface defining a socket designed to engage the substantially hemispherical head of the screw such that the head of the screw is prevented from passing therethrough and such that the screw may be rotated therein to adjust the angle between the axis of the screw and the axis of the bore, said coupling element further comprising a pair of opposing upper channels formed in the top of said coupling element such that an elongated rod may be received therein and a pair of opposing lower channels formed in the bottom of said coupling element designed to allow the shaft of the screw to move therethrough, the lower channels being designed such that the angle between the axis of the screw and the axis of the coupling element can be adjusted to at least 90 degrees, and a securing nut, mateable with said internal threading and entirely within at least the radial boundaries of the axial bore of said coupling element, the nut having an engaging portion designed to engage the elongated rod, the engaging portion further comprising a plurality of engaging teeth designed to frictionally lock the rod within the upper channel of the coupling element.

10. A low profile vertebral alignment/fixation system as described in claim 9, wherein the angles between the axis of the screw and the axis of the coupling element can be adjusted to at least 100 degrees.

11. A low profile vertebral alignment/fixation system as described in claim 9, wherein the system components are made of stainless steel.

12. A low profile vertebral alignment/fixation system as described in claim 9, wherein the recess is designed to receive a screw driver from the group consisting of: flat-headed, phillips head, allen wrench, and square headed.

13. A low profile vertebral alignment/fixation system as described in claim 9, wherein the nut further comprises an axial recess identical to the recess disposed on the screw head.

14. A low profile vertebral alignment/fixation system as described in claim 13, wherein the nut recess is designed to receive a screw driver from the group consisting of: flat-headed, phillips head, allen wrench, and square headed.

15. A low profile vertebral alignment/fixation system as described in claim 9, wherein the screw further comprises a slotted groove disposed longitudinally along the tip and designed to allow the screw to be self-tapped.

16. A low profile vertebral alignment/fixation system as described in claim 9, further comprising at least one piece of fixation hardware designed to engage the at least one vertebral alignment/fixation assembly, the fixation hardware selected from the group consisting of: crosslinks, clamps, plates and rods.

17. A low profile vertebral alignment/fixation method comprising:

providing a vertebral alignment/fixation system as described in claim 9;

inserting the screw into the coupling element such that the head of the screw engages the socket of the coupling element;

driving the screw into a vertebral body;

inserting a rod into the upper channels of the coupling unit;

angularly aligning the coupling unit and rod with the vertebral body;

tightening a securing nut into the coupling unit such that the engaging portion of the nut pressingly engages the rod, forcing the rod into the head of the screw thereby fixedly attaching the rod within the coupling element and preventing the coupling element from being angularly rotated with respect to the screw.

18. A low profile vertebral alignment/fixation method comprising utilizing a vertebral alignment/fixation system as described in claim 9 to align at least one vertebral body.

* * * * *

UNITED STATES PATENT AND TRADEMARK OFFICE
CERTIFICATE OF CORRECTION

PATENT NO. : 6,981,973 B2  Page 1 of 1
APPLICATION NO. : 10/639119
DATED : January 3, 2006
INVENTOR(S) : McKinley It is certified that error appears in the above-identified patent and that said Letters Patent is hereby corrected as shown below:

On the Title Page

Item (57) Abstract, line 10          Delete "enabling",
                                      Insert --enables--

Signed and Sealed this

Sixth Day of February, 2007

JON W. DUDAS
*Director of the United States Patent and Trademark Office*